United States Patent
Li et al.

(10) Patent No.: US 10,159,407 B2
(45) Date of Patent: Dec. 25, 2018

(54) ANTERIOR EYE TOMOGRAPHIC IMAGE CAPTURING APPARATUS

(71) Applicant: Tomey Corporation, Nagoya-shi (JP)

(72) Inventors: Fushi Li, Nagoya (JP); Keiichiro Okamoto, Nagoya (JP); Kenichi Hayashi, Nagoya (JP)

(73) Assignee: Tomey Corporation, Nagoya-Shi (JP)

( * ) Notice: Subject to any disclaimer, the term of this patent is extended or adjusted under 35 U.S.C. 154(b) by 191 days.

(21) Appl. No.: 15/296,598

(22) Filed: Oct. 18, 2016

(65) Prior Publication Data

US 2017/0105617 A1 Apr. 20, 2017

(30) Foreign Application Priority Data

Oct. 19, 2015 (JP) ................................. 2015-205179

(51) Int. Cl.
| | | |
|---|---|---|
| *A61B 3/14* | (2006.01) | |
| *A61B 3/10* | (2006.01) | |
| *A61B 3/00* | (2006.01) | |
| *A61B 3/103* | (2006.01) | |
| *A61B 8/10* | (2006.01) | |
| *A61B 3/117* | (2006.01) | |

(52) U.S. Cl.
CPC ............ *A61B 3/102* (2013.01); *A61B 3/0025* (2013.01); *A61B 3/103* (2013.01); *A61B 3/1005* (2013.01); *A61B 3/117* (2013.01); *A61B 8/10* (2013.01)

(58) Field of Classification Search
CPC ....... A61B 3/0025; A61B 3/0041; A61B 3/10; A61B 3/14; A61B 3/102; A61B 3/103; A61B 3/117; A61B 3/1005; A61B 3/1173; A61B 8/085; A61B 8/10; A61B 8/4416; A61B 8/5223; A61F 2/16; A61F 2/1605; G06T 7/0014
USPC ......... 351/206, 212, 246; 382/131; 600/452; 606/107

See application file for complete search history.

(56) References Cited

U.S. PATENT DOCUMENTS

| | | |
|---|---|---|
| 8,967,810 B1 | 3/2015 | Prager et al. |
| 9,060,717 B2 | 6/2015 | Bailey et al. |
| 9,265,411 B2 | 2/2016 | Chen et al. |

(Continued)

FOREIGN PATENT DOCUMENTS

| | | |
|---|---|---|
| EP | 2865324 A1 | 4/2015 |
| JP | 2013-094410 A | 5/2013 |

(Continued)

*Primary Examiner* — Mustak Choudhury
(74) *Attorney, Agent, or Firm* — Shumaker, Loop & Kendrick, LLP (57) ABSTRACT

An anterior eye tomographic image capturing apparatus determining a power of an IOL (intraocular lens) is configured to acquire a tomographic image of an anterior eye along a straight line passing through a corneal apex of the anterior eye; identify a corneal apex position of the anterior eye, an equator position of a crystalline lens of the anterior eye, and a SS (scleral spur) position of the anterior eye based on the tomographic image; calculate an ELP (estimated lens position) based on a first distance from the corneal apex position to the SS position in a direction of a visual axis and a second distance from the SS position to the equator position in the direction of the visual axis; and determine the power of the IOL by using the ELP.

7 Claims, 10 Drawing Sheets

(56) References Cited

U.S. PATENT DOCUMENTS

| | | | |
|---|---|---|---|
| 2010/0134763 A1* | 6/2010 | Von Bunau | A61B 3/0025 351/246 |
| 2013/0107208 A1 | 5/2013 | Endo et al. | |
| 2013/0258283 A1 | 10/2013 | Goto et al. | |
| 2015/0092162 A1* | 4/2015 | Tsunehiro | A61B 3/0025 351/206 |
| 2015/0150447 A1 | 6/2015 | Huang et al. | |
| 2016/0074007 A1 | 3/2016 | Fedor | |

FOREIGN PATENT DOCUMENTS

| | | |
|---|---|---|
| JP | 2015-066083 A | 4/2015 |
| WO | 2013-188885 A1 | 12/2013 |

\* cited by examiner

Normal-angled Eye Before Cataract Surgery $ELP1 = CCT1 + SPD1 + a1 (+\alpha)$

FIG.8B

Narrow-angled Eye Before Cataract Surgery $ELP2 = CCT2 + SPD2 + a2$

FIG.8C

After Cataract Surgery $ELP3 \fallingdotseq ELP1$
$ELP3 \fallingdotseq ELP2$

ANTERIOR EYE TOMOGRAPHIC IMAGE CAPTURING APPARATUS

TECHNICAL FIELD

The present disclosure relates to an anterior eye tomographic image capturing apparatus configured to determine a power of an intraocular lens implanted by a cataract surgery by using a tomographic image of an anterior eye.

DESCRIPTION OF RELATED ART

In recent years, as an examination apparatus used for ophthalmologic examination, an optical coherence tomographic image capturing apparatus which captures a tomographic image of a subjected eye (eyeball) of a subject by an optical coherence tomography (OCT) is provided.

The optical coherence tomographic image capturing apparatus uses a time domain OCT called a time domain system which acquires a tomographic image while mechanically changing an optical path length of reference light by moving a mirror, a spectrum domain OCT called a Fourier domain system which detects spectrum information by using a spectroscope and acquires a tomographic image, or an optical frequency sweeping OCT which detects a spectrum interference signal by using a wavelength scanning light source and acquires a tomographic image.

Generally, in the OCT, a two-dimensional tomographic image is acquired by scanning measurement light one-dimensionally relative to the subjected eye (B-scan), and then a three-dimensional image is obtained by acquiring two-dimensional tomographic images repeatedly while displacing scanning position relative to the subjected eye (C-scan).

Figure 4A:
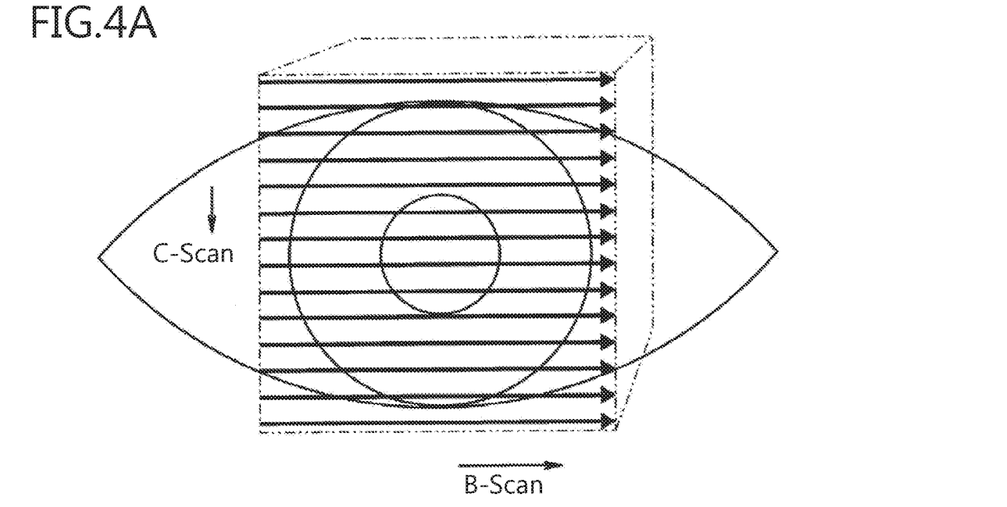
FIG. 4A is a diagram for explaining a raster scan method in OCT.
Figure 4B:
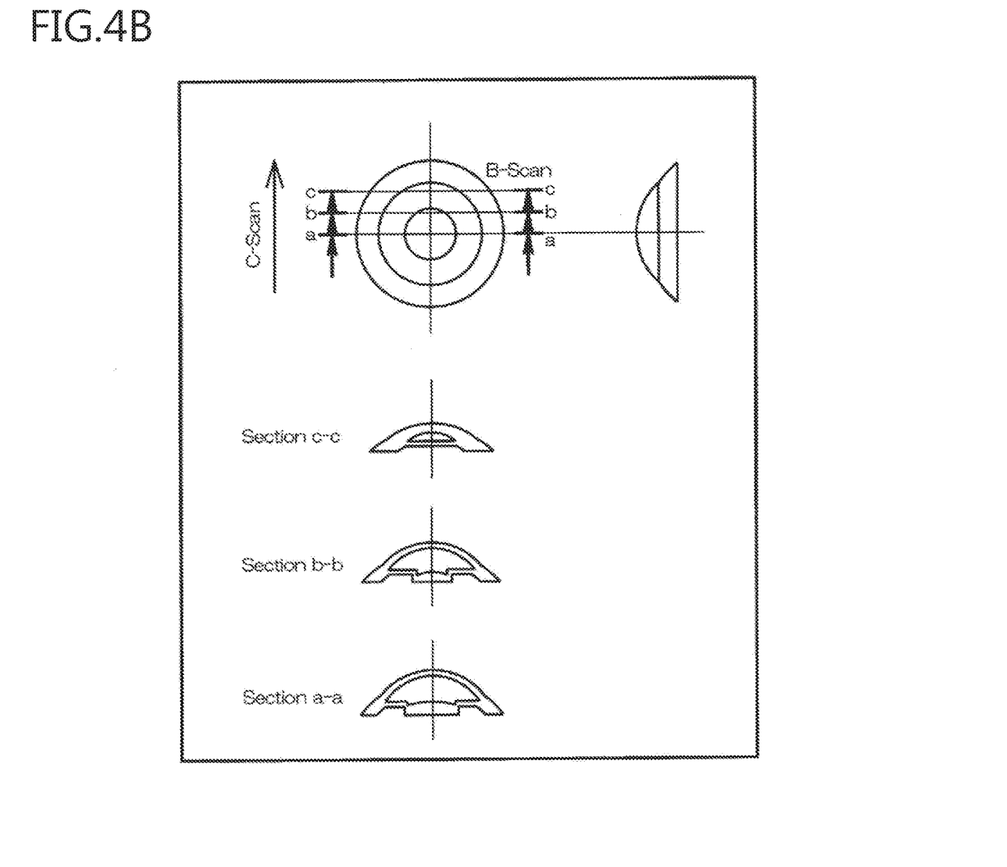
FIG. 4B is a diagram for explaining the raster scan method in OCT.

As a scanning method, there is a method called raster scan as shown in FIG. 4A. In the raster scan, a one-dimensional scan along a scan line extending horizontally (B-scan) is performed repeatedly while moving in a vertical direction to other scan lines (C-scan) to capture a three-dimensional image of an eyeball. Due to this, as shown in FIG. 4B, tomographic images along respective scan lines can be obtained.

Figure 5A:
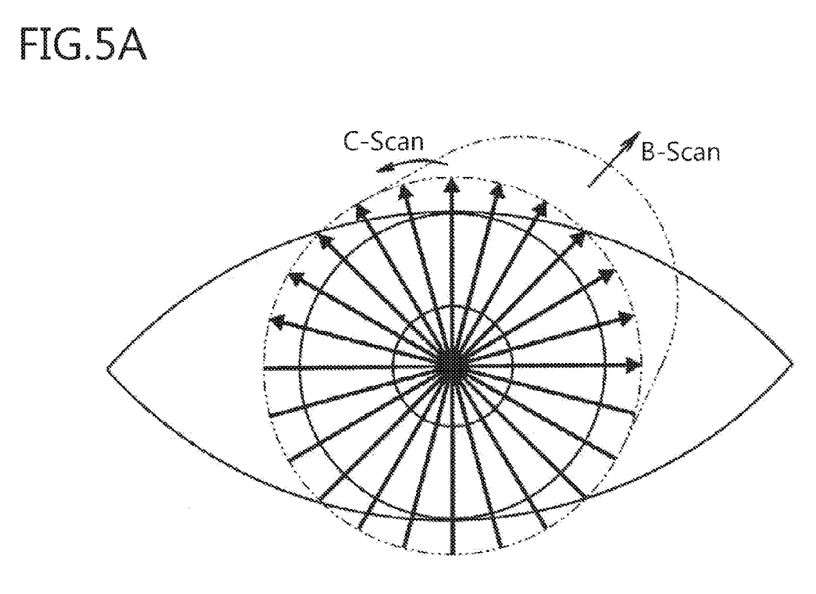
FIG. 5A is a diagram for explaining a radial scan method in OCT.
Figure 5B:
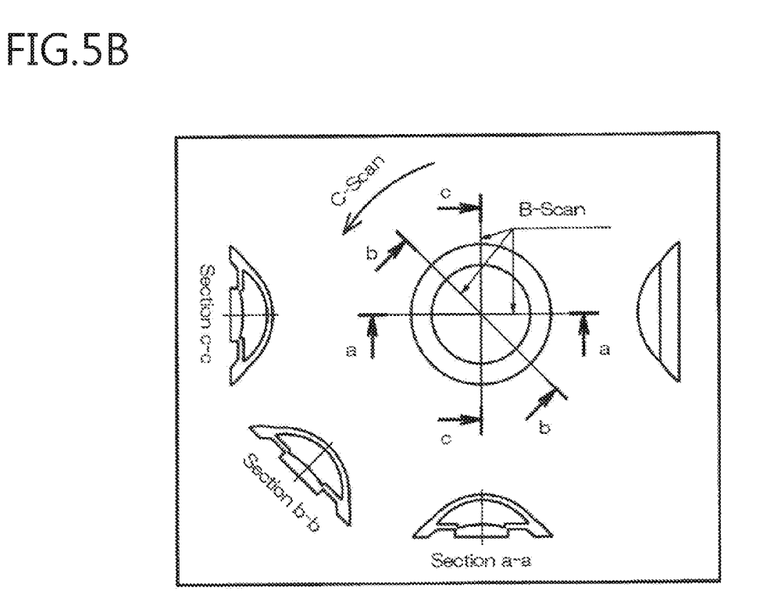
FIG. 5B is a diagram for explaining the radial scan method in OCT.

As another scanning method, there is a method called a radial scan as shown in FIG. 5A. In the radial scan, a one-dimensional scan along a scan line extending radially (B-scan) is performed repeatedly while moving in a circumferential direction to other scan lines (C-scan). Due to this, as shown in FIG. 5B, tomographic images along respective scan lines can be obtained.

Eye characteristics data, such as a corneal curvature (kerato value), a length of eye axis, and the like, is acquired to determine a power of an intraocular lens (IOL) to be implanted in a cataract surgery. Then, the IOL power is calculated based on the acquired eye characteristics data using an IOL calculating formula that has been created empirically or logically. SRK formula, SRK/T formula, and the like are well known as the IOL calculating formula.

In recent years, an anterior eye tomographic image capturing apparatus employing the OCT technique has been used for determining the IOL power. For example, Japanese Patent Application Publication No. 2013-94410 discloses a method for determining the IOL power with higher accuracy by using acquired tomographic images of an anterior eye.

In Japanese Patent Application Publication No. 2013-94410, a distance from a front surface of a crystalline lens to a contact point of a Zinn's zonule and the crystalline lens is set as an offset distance, based on the tomographic images of the anterior eye. Then, an estimated lens position (ELP) is calculated by adding the offset distance to an anterior chamber depth (ACD) of the eye (a distance from an apex of a corneal epithelium to the front surface of the crystalline lens). Thereafter, the IOL power is calculated and determined using the ELP.

A position of a support portion of the IOL is similar to a position of the contact point of the Zinn's zonule and the crystalline lens. Due to this, by using the distance from the front surface of the crystalline lens to the contact point of the Zinn's zonule and the crystalline lens as an offset value, a highly accurate ELP can be calculated. Due to this, a highly accurate IOL power can be determined.

SUMMARY

The method disclosed in Japanese Patent Application Publication No. 2013-94410 is considered effective, if a patient's eye has an angle area that is normal or an open angle. However, if the patient's eye has a narrow angle (due to a closed angle and the like), a crystalline lens of the eye is located anteriorly compared to a case where the eye has the normal angle or the open angle. In this case, a value of ACD of the narrow-angled eye is smaller compared to the case where the eye has the normal angle or the open angle. However, it is known as a postoperative finding that if an IOL is implanted into such a narrow-angled eye, its narrow angle will be eliminated and become normal.

Thus, in a case where the method disclosed in Japanese Patent Application Publication No. 2013-94410 in which the ELP is calculated using the preoperative ACD is employed, depending on a state of an angle of a patient's eye, there is a problem that the calculated ELP and an actual postoperative ACD largely differ from each other.

The present disclosure is to solve the aforementioned problem and aims to disclose an apparatus configured to determine an IOL power regardless of a preoperative state of an angle of a subjected eye by extracting a position of a scleral spur (SS) on an acquired anterior eye tomographic image (B-scan image) by image analysis or the like, and by calculating an ELP based on the extracted SS position.

To achieve the aforementioned aim, an anterior eye tomographic image capturing apparatus configured to determine a power of an IOL comprises a processor; and a memory storing computer-readable instructions therein, wherein the computer-readable instructions, when executed by the processor, cause the apparatus to perform acquiring a tomographic image of an anterior eye along a straight line passing through a corneal apex of the anterior eye; identifying a corneal apex position of the anterior eye, an equator position of a crystalline lens of the anterior eye, and a SS position of the anterior eye based on the tomographic image; and calculating an ELP based on a first distance from the corneal apex position to the SS position in a direction of a visual axis and a second distance from the SS position to the equator position in the direction of the visual axis.

The SS position does not change regardless of a patient's eye being a normal-angled eye or a narrow-angled eye, and before or after an implantation of the IOL. Further, it is known from findings that the SS position is close to a position of an apex of a front surface of the crystalline lens. The anterior eye tomographic image capturing apparatus identifies the corneal apex position, the SS position, and the equator position of the crystalline lens from the tomographic image of the anterior eye along the straight line passing through the corneal apex. Then, the anterior eye tomographic image capturing apparatus calculates the ELP based on the first distance from the corneal apex position to the SS position and the second distance from the SS position to the equator position of the crystalline lens. Due to this, the calculated ELP does not depend on a state of the angle of the patient's eye (normal-angled eye or narrow-angled eye). Thus, there is no risk of the calculated ELP having a large difference compared to the ELP calculated using the ACD as disclosed in Japanese Patent Application Publication No. 2013-94410. Accordingly, a highly accurate ELP can be calculated correctly regardless of the angle state of the patient's eye.

The identifying may comprise identifying a thickness of the crystalline lens in the direction of the visual axis at a position that overlaps with the visual axis, a first curvature of a front surface of the crystalline lens, and a second curvature of a rear surface of the crystalline lens based on the tomographic image, and identifying the equator position of the crystalline lens based on the thickness of the crystalline lens, the first curvature, and the second curvature.

A postoperative position of an implanted IOL is placed slightly below the equator position of the preoperative crystalline lens. The equator position of the crystalline lens can be identified by obtaining the thickness and the curvatures of the front and rear surfaces of the preoperative crystalline lens from the tomographic image of the anterior eye. The ELP is calculated based on the identified equator position of the crystalline lens, the second distance of the SS, and the first distance, by which a further highly accurate ELP can be obtained.

The identifying may comprise identifying a crystalline lens nucleus of the crystalline lens based on the tomographic image, and identifying the equator position of the crystalline lens based on the crystalline lens nucleus.

The equator position can be identified from a shape of the preoperative crystalline lens nucleus identified from the tomographic image of the anterior eye. Due to this, a further highly accurate ELP can be obtained.

The identifying may comprise identifying a thickness of the crystalline lens in the direction of the visual axis at a position that overlaps with the visual axis, a first curvature of a front surface of the crystalline lens, and a second curvature of a rear surface of the crystalline lens based on the tomographic image, identifying a first equator position based on the thickness of the crystalline lens, the first curvature, and the second curvature, identifying a crystalline lens nucleus of the crystalline lens based on the tomographic image, identifying a second equator position based on the crystalline lens nucleus, and identifying the equator position based on at least one of the first equator position and the second equator position.

Depending on a state of the crystalline lens or pupil, there may be a case where there is a large difference between the first equator position identified based on the thickness and the curvatures of the front and rear surfaces of the crystalline lens, and the second equator position identified based on the crystalline lens nucleus. In this case, there may be a large difference between a distance from the SS to the first equator position and a distance from the SS to the second equator position. In this case, one of the first and second equator positions which is deemed appropriate from the state of the crystalline lens may be identified as the equator position of the crystalline lens, and a distance from the identified equator position to the SS may be adopted. Alternatively, a simple average distance of the distance from the SS to the first equator position and the distance from the SS to the second equator position may be adopted.

The identifying may comprise identifying an implantation position of the IOL in a case where the IOL is to be implanted to the crystalline lens of the anterior eye. In this case, the calculating may comprise calculating a third distance from the IOL to the equator position in the direction of the visual axis, and calculating the ELP using the first distance, the second distance, and the third distance.

A postoperative position at which the IOL is stably positioned can be identified from a lens constant provided by a manufacturer of the IOL. The ELP can be determined by calculating the third distance from the postoperative IOL position to the equator position of the crystalline lens and using the third distance. In this case, a further highly accurate ELP can be obtained.

As aforementioned, according to the present disclosure, since an appropriate ELP can be calculated regardless of a preoperative state of an angle of the subjected eye, a further highly accurate IOL power can be determined.

EMBODIMENTS

Hereinbelow, an embodiment according to the present disclosure will be described with reference to FIGS. 1 to 3. Notably, an anterior eye optical coherence tomographic image capturing apparatus, which is a kind of an anterior eye tomographic image capturing apparatus, is used in the present embodiment. However, the present disclosure is not limited to the anterior eye optical coherence tomographic image capturing apparatus and any apparatus capable of capturing tomographic images of an anterior eye, such as an ultrasound imaging apparatus using ultrasound and the like, can be employed.

Figure 1:
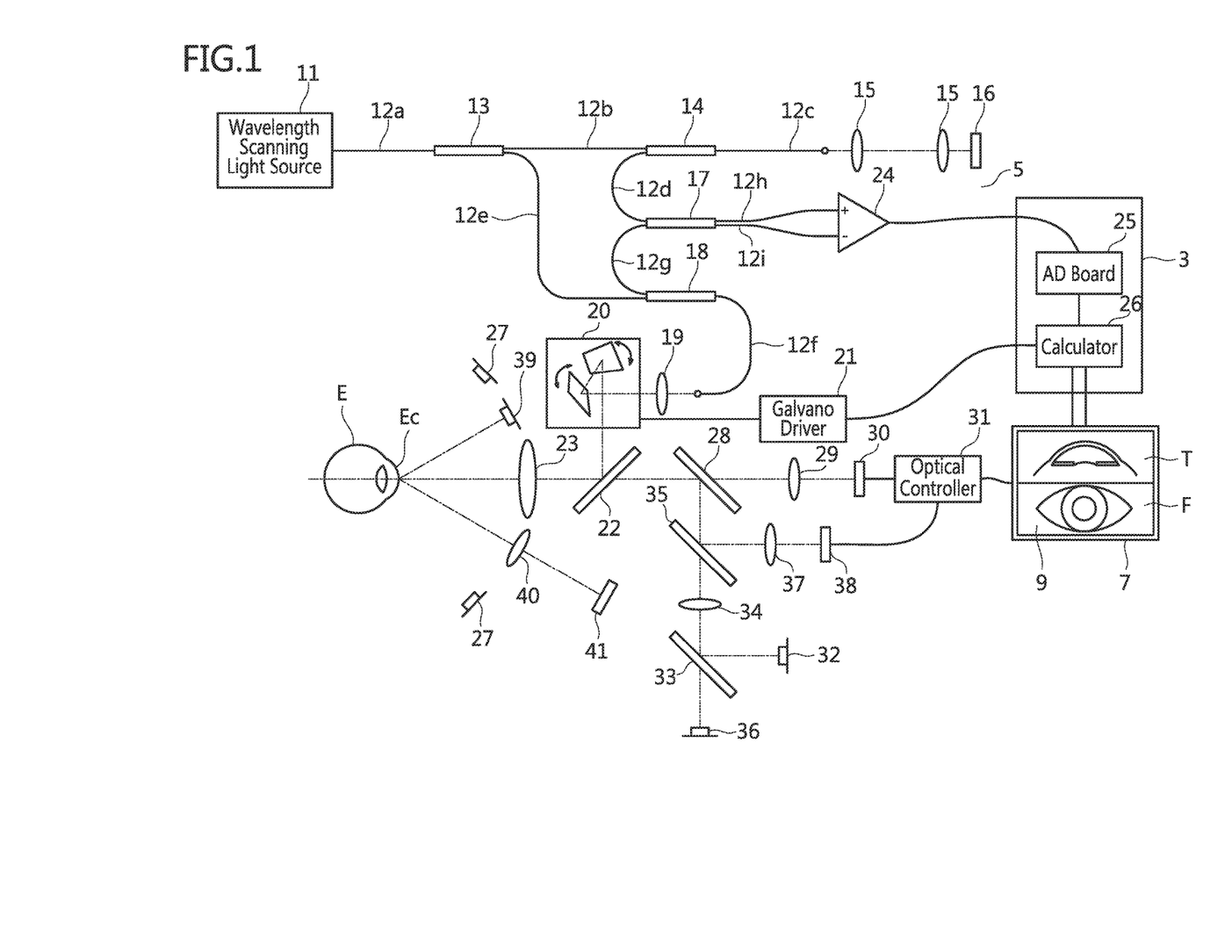
FIG. 1 is a diagram showing configurations of optical systems of an anterior eye optical coherence tomographic image capturing apparatus, which is a kind of an anterior eye tomographic image capturing apparatus, of an embodiment of the present disclosure.
Figure 2:
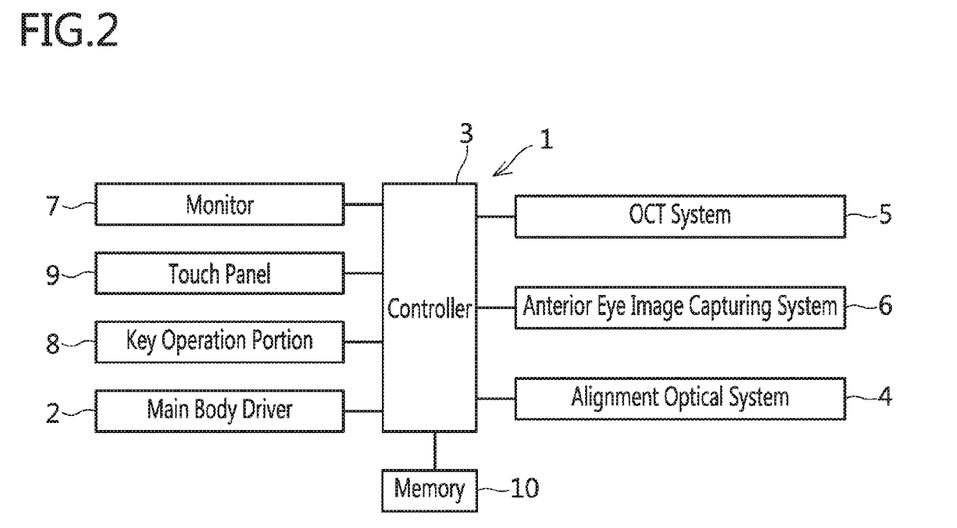
FIG. 2 is a block diagram schematically showing an electrical configuration of the anterior eye optical coherence tomographic image capturing apparatus.
Figure 3:
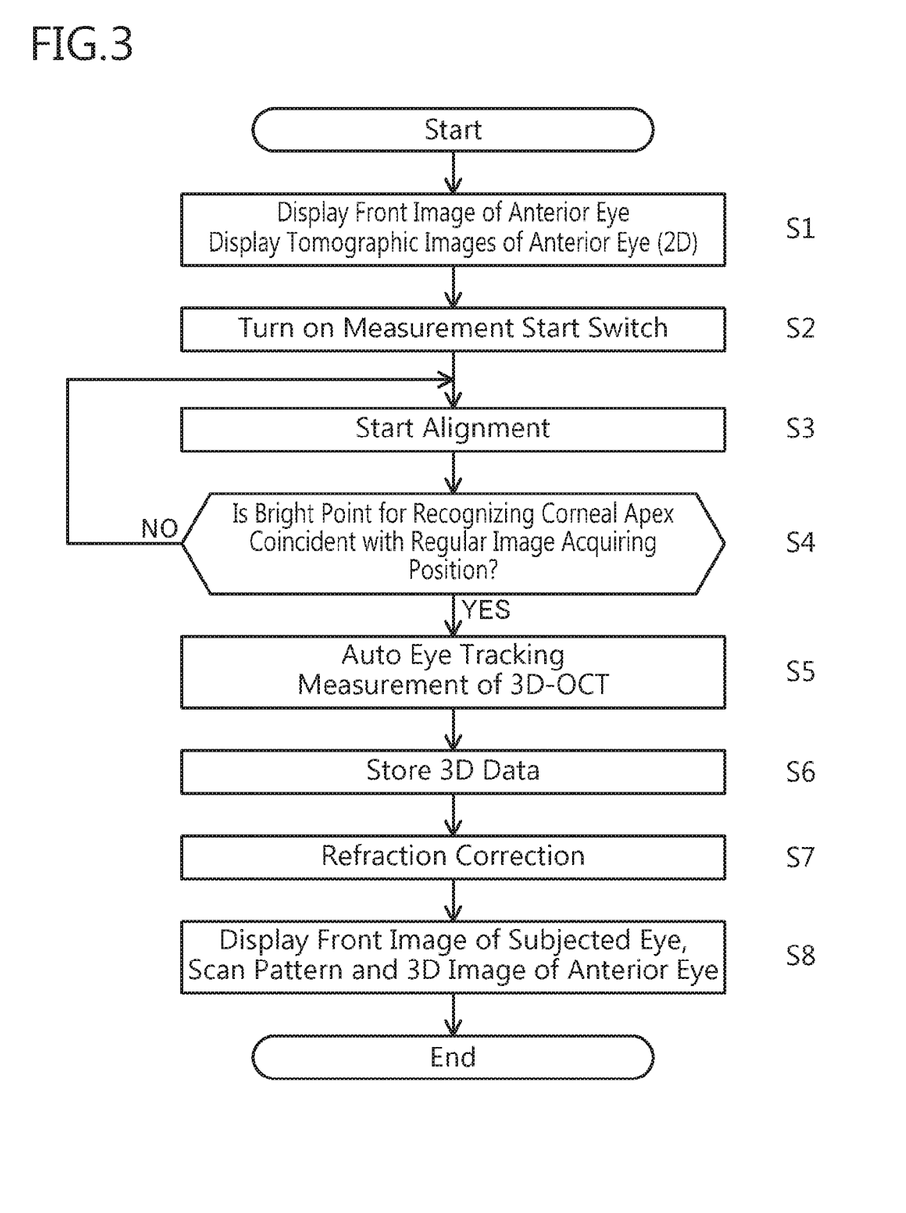
FIG. 3 is a flowchart showing a procedure of a tomographic image capturing process executed by a controller.

FIG. 2 schematically shows an electrical configuration of an anterior eye optical coherence tomographic image capturing apparatus 1 (hereinbelow, referred to as "optical coherence tomographic apparatus 1") according to the present embodiment. Notably, the optical coherence tomographic apparatus 1 is used for ophthalmologic examinations for an anterior eye Ec of a subject's eyeball (subjected eye E) (see FIG. 1) such as measurements of an angle of the eye, a curvature of a cornea, a distribution of corneal thickness, an ACD, and the like, as well as for an ophthalmologic diagnosis in which a tomographic image of the anterior eye including the cornea, iris, and crystalline lens is displayed on a monitor or the like. The optical coherence tomographic apparatus 1 captures tomographic images of the anterior eye Ec of the subjected eye E by Optical Coherence Tomography (OCT).

Here, although not shown, a main body of the optical coherence tomographic apparatus 1 (hereinbelow, referred to as "main body of the apparatus 1") is supported so as to be movable in an X direction (left-and-right direction), in a Y direction (up-and-down direction), and in a Z direction (front-and-rear direction) relative to a holding table. A chin support and a forehead pad are fixed relative to the holding table on a front face side (subject side) of the main body of the apparatus 1. When the subject puts the chin on the chin support and puts the forehead against the forehead pad, the subject's eye (subjected eye E) comes to be positioned in front of an inspection window for capturing images (through which light comes in and goes out) which is provided in a front face of the main body of the apparatus 1.

As shown in FIG. 2, the optical coherence tomographic apparatus 1 comprises a main body driver 2 configured to move the main body of the apparatus 1 relative to the holding table freely in each of the X, Y, and Z directions. The main body driver 2, although details thereof are omitted, comprises a well-known configuration including an X-direction movement motor, a Y-direction movement motor, a Z-direction movement motor, and the like, and is controlled by a controller 3. As described later, the main body driver 2 and the controller 3, together with an alignment optical system 4, configure an alignment unit and an auto eye tracking unit.

As shown in FIG. 2, the main body of the apparatus 1 comprises the controller 3 which includes a microcomputer including a CPU, a memory, and the like and is configured to perform overall control of the optical coherence tomographic apparatus 1, an OCT system 5 serving as a tomographic image acquisition unit for acquiring tomographic images of the anterior eye Ec, an anterior eye image capturing system 6 which configures an image capturing unit for capturing a front image of the subjected eye E, and the alignment optical system 4. As aforementioned, the alignment optical system 4 configures the alignment unit and the auto eye tracking unit, as well as a corneal apex position detecting unit. Details of the OCT system 5, the anterior eye image capturing system 6, and the alignment optical system 4 will be described later.

Further, the main body of the apparatus 1 comprises a monitor 7 which is positioned on a rear face side (examiner's side) of the main body of the apparatus 1 and serves as a display device configured to display a front image of the subjected eye and the like, and a key operation portion 8 for the examiner (operator) to perform various kinds of operations. Although not shown, the key operation portion 8 comprises a measurement start switch and the like. Further, in the present embodiment, a touch panel 9 functioning as various operation portions is provided on a screen of the monitor 7. Notably, a memory 10 storing image data of captured three-dimensional images and the like is connected to the controller 3.

FIG. 1 shows configurations of the aforementioned optical systems, that is, configurations of the OCT system 5, the anterior eye image capturing system 6, and the alignment optical system 4. Hereinbelow, these configurations will each be described. The OCT system 5 is configured to acquire tomographic images (cross sectional images) of the anterior eye Ec by OCT. In the present embodiment, Fourier domain (optical frequency sweep) system is employed in which a wavelength scanning light source 11 which performs scans while temporally changing a wavelength is used.

Light output from the wavelength scanning light source 11 is input to a first fiber coupler 13 through an optical fiber 12a. The light input to the first fiber coupler 13 is demultiplexed into reference light and measurement light, for example at a ratio of 1:99, in the first fiber coupler 13, and each light is output. The reference light is input to an input portion of a first circulator 14 through an optical fiber 12b, output from an input-output portion of the first circulator 14, passes through an optical fiber 12c, is output from an end of the optical fiber 12c, passes through a plurality of collimator lenses 15, and then enters a reference mirror 16.

The reference light reflected by the reference mirror 16, again, passes through the plurality of the collimator lenses 15, is input from the end of the optical fiber 12c, passes through the optical fiber 12c, and is input to the input-output portion of the first circulator 14. Then, the reference light output from an output portion of the first circulator 14 passes through an optical fiber 12d and is input to a first input portion of a second fiber coupler 17.

Meanwhile, the measurement light output from the first fiber coupler 13 is input to an input portion of a second circulator 18 through an optical fiber 12e. Further, the measurement light is output from an input-output portion of the second circulator 18, passes through an optical fiber 12f, and is output from an end of the optical fiber 12f. The measurement light output from the end of the optical fiber 12f passes through a collimator lens 19 and is input to a Galvano scanner 20. The Galvano scanner 20 is configured to scan the measurement light and driven by a Galvano driver 21.

The measurement light output from the Galvano scanner 20 is reflected at 90 degrees by a hot mirror 22 which reflects light of which wavelength is on a long-wavelength side and allows light of which wavelength is on a short-wavelength side to pass therethrough, passes through an objective lens 23, is output from the inspection window, and then enters the subjected eye E. The measurement light which has entered the subjected eye E is reflected at respective structural parts of the anterior eye Ec (cornea, anterior chamber, iris, crystalline lens, and the like). The reflected light enters the inspection window, and in an inverse order as the order mentioned above, passes through the objective lens 23, the hot mirror 22, the Galvano scanner 20, and the collimator lens 19, and is input to the end of the optical fiber 12f. The reflected light input to the end of the optical fiber 12f passes through the optical fiber 12f, is input to the input-output portion of the second circulator 18, is output from an output portion of the second circulator 18, passes through an optical fiber 12g, and then is input to a second input portion of the second fiber coupler 17.

In the second fiber coupler 17, the reflected light from the anterior eye Ec and the reference light input through the optical fiber 12d are multiplexed, for example at a ratio of 50:50, and a signal thereof passes through an optical fiber 12h and an optical fiber 12i, and is input to a detector 24. In the detector 24, interference of every wavelength is measured. The measured interference signals are input to an AD board 25 provided in the controller 3. Further, in a calculator 26 provided in the controller 3, processing such as Fourier transform is executed to the interference signals, and then tomographic images of the anterior eye Ec along scan lines are acquired.

As mentioned in detail later, a scanning pattern of the measurement light in the Galvano scanner 20, a direction of the scan lines (B-scan) in other words, is set in the controller 3. That is, the Galvano driver 21 controls the Galvano scanner 20 according to a command signal from the controller 3 (the calculator 26). Notably, data of the acquired tomographic images of the anterior eye Ec is stored in the memory 10 after necessary refraction correction has been performed. Further, as shown in FIG. 1 schematically, a tomographic image T can be displayed on the monitor 7.

Next, the anterior eye image capturing system 6 comprises two illumination light sources 27, the objective lens 23, the hot mirror 22, a cold mirror 28, an imaging lens 29, a CCD camera 30, and an optical controller 31. The two illumination light sources 27 are configured to radiate illumination light within a visible light range to a front surface of the subjected eye E. The light reflected by the subjected eye E is input to the CCD camera 30 from the inspection window through the objective lens 23, the hot mirror 22, the cold mirror 28, and the imaging lens 29. Due to this, a front image F of the subjected eye E is captured. Data of the captured image is image-processed by the optical controller 31, and then displayed on the monitor 7.

The alignment optical system 4 comprises a vision-fixation lamp optical system for suppressing a movement of the eyeball (subjected eye E) as much as possible by making the subject stare at a vision-fixation lamp, an XY directional position detecting system for detecting positions of the subjected eye E (an corneal apex) in X and Y directions (displacements in the up-and-down direction and the right-and-left direction relative to the main body of the apparatus 1), and a Z directional position detecting system for detecting a position of the subjected eye E (the corneal apex) in the back-and-forth direction (Z direction).

The vision-fixation lamp optical system comprises a vision-fixation lamp 32, a cold mirror 33, a relay lens 34, a half mirror 35, the cold mirror 28, the hot mirror 22, the objective lens 23, and the like. Due to this, light output from the vision-fixation lamp 32 (for example, green light) enters the subjected eye E from the inspection window after passing through the cold mirror 33, the relay lens 34, the half mirror 35, the cold mirror 28, the hot mirror 22, and the objective lens 23 in this order.

The XY directional position detecting system comprises an XY position detecting light source 36, the cold mirror 33, the relay lens 34, the half mirror 35, the cold mirror 28, the hot mirror 22, the objective lens 23, an imaging lens 37, a position sensor 38, and the like. Alignment light for position detection is output from the XY position detecting light source 36. The alignment light enters the anterior eye Ec (the cornea) of the subjected eye E after passing through the cold mirror 33, the relay lens 34, the half mirror 35, the cold mirror 28, the hot mirror 22, the objective lens 23, and the inspection window.

Since a corneal surface of the subjected eye E has a spherical shape, the alignment light is reflected on the corneal surface so as to form a bright point image on an inner side of the corneal apex of the subjected eye E. The reflected light (bright point) from the corneal surface enters from the inspection window. The reflected light from the corneal apex is input to the position sensor 38 after passing through the objective lens 23, the hot mirror 22, the cold mirror 28, the half mirror 35, and the imaging lens 37. A position of the bright point is detected by the position sensor 38. Due to this, a position of the corneal apex (position in X and Y directions) is detected. Notably, the bright point is displayed on the image captured by the CCD camera 30 (the image displayed on the monitor 7) as well.

A detection signal of the position sensor 38 is input to the optical controller 31 and the controller 3. At this occasion, the position sensor 38 and the anterior eye image capturing system 6 (the CCD camera 30 and the monitor 7) are aligned with each other, and at the same time, a predetermined (regular) image acquiring position of the corneal apex (a position to be followed upon acquiring tomographic images) is set. For example, a point that is coincident with a center position of the image captured by the CCD camera 30 (a center position of the screen of the monitor 7) is regarded as the regular image acquiring position of the corneal apex. The controller 3, based on the detection by the position sensor 38, finds positional displacement amount of the detected corneal apex (bright point) in the X direction and the Y direction (positional displacement amount from the center of the screen of the monitor 7) relative to the regular image acquiring position.

The Z directional position detecting system comprises a Z position detecting light source 39, an imaging lens 40, and a line sensor 41. The Z position detecting light source 39 radiates light for detection (slit light or spot light) to the subjected eye E obliquely relative to the subjected eye E. The light reflected obliquely by the cornea enters the line sensor 41 through the imaging lens 40. Depending on a position of the subjected eye E in the back-and-forth direction (Z direction) relative to the main body of the apparatus 1, an incident position of the reflected light which enters the line sensor 41 varies. Due to this, by detecting the incident position, the position (distance) of the subjected eye E in the Z direction relative to the main body of the apparatus 1 is detected.

A detection signal of the line sensor 41 is input to the controller 3. In the controller 3, an appropriate position (distance) of the subjected eye E (cornea) in the Z direction relative to the main body of the apparatus 1 has been predetermined Due to this, based on the detection by the line sensor 41, displacement amount of the subjected eye E in the Z direction relative to the appropriate position can be obtained.

Further, based on the positional displacement amount of the corneal apex (bright point) in the X direction and the Y direction detected by the XY directional position detecting system 56 and the positional displacement amount of the subjected eye E in the Z direction detected by the Z directional position detecting system 58, the controller 3 controls the main body driver 2 and moves the main body of the apparatus 1 relative to the holding table so that those positional displacement amounts become zero. The controller 3 is configured to move the main body of the apparatus 1 relative to the holding table so as to make the position of the corneal apex coincident with the predetermined image acquiring position at a time of starting to acquire tomographic images. Further, the controller 3 moves the main body of the apparatus 1 so as to track the corneal apex so that a positional relationship between the corneal apex and the main body of the apparatus 1 is maintained constant while tomographic images are being acquired as well. Due to this, the alignment unit and the auto eye tracking unit are configured.

Next, an operation of the optical coherence tomographic apparatus 1 will be described with reference to FIG. 3. A flowchart in FIG. 3 shows a procedure of a processing executed by the controller 3 when tomographic images of the anterior eye Ec of the subjected eye E are captured.

The processing for capturing tomographic images of the anterior eye Ec is started (an anterior eye tomographic image capturing program is initiated) under a state where the subject puts the chin on the chin support as well as puts the forehead against the forehead pad, and the subjected eye E is positioned in front of the inspection window of the main body of the apparatus 1. First, in step S1, the controller 3 displays on the monitor 7 a current front image F of the subjected eye E which has been captured by the anterior eye image capturing system 6 (the CCD camera 30) as well as a current tomographic image T of the anterior eye Ec which has been scanned along a scan line extending horizontally and passing through the center of the screen (see FIG. 1). However, at this point of time, data of the front image F and the tomographic image T are not imported into the memory 10.

Thereafter, upon detecting that the examiner has turned on the measurement start switch (step S2), the controller 3 starts alignments in the X, Y, Z directions by the alignment optical system 4 and the like in step S3. The controller 3 finishes the alignments in a case where a bright point for recognizing the corneal apex is coincident with the regular image acquiring position (YES in step S4). Then, in step S5, the controller 3 executes processing of acquiring tomographic images of the anterior eye Ec by the OCT system 5. During the processing of acquiring the tomographic images, auto eye-tracking functions, and thus the main body of the apparatus 1 is moved by the alignment optical system 4 and the like so as to track the corneal apex such that the bright point for recognizing the corneal apex is constantly coincident with the regular image acquiring position (a center position of the image captured by the CCD camera 30).

In the present embodiment, the processing of acquiring the tomographic images in step S5 is executed by a radial scan method shown in FIG. 5A, 5B. Due to this, the tomographic images of an entire region of the anterior eye Ec are acquired. That is, the tomographic images are scanned with a B-scan direction as a radial direction and a C-scan direction as a circumferential direction. At this occasion, even if the subjected eye E moves, the positional relationship between the main body of the apparatus 1 and the subjected eye E is maintained constant by the auto eye tracking. Due to this, it is possible to prevent the scan lines from deviating from straight lines passing through the corneal apex. In step S6, the controller 3 imports data of the acquired (captured) tomographic images into the memory.

In step S7, the controller 3 performs the refraction correction relative to the data of each tomographic image. Since the measurement light is refracted at the cornea having an almost-spherical shape (at an interface between the corneal surface and the anterior chamber), the crude tomographic images have distortions. Thus, the data of the tomographic images is corrected for that cornea refraction. The image data after the refraction correction is stored in the memory 10.

In step S8, the controller 3 displays on the monitor 7 the front image F of the subjected eye E, a scan pattern at the time of acquiring the tomographic images, and a three-dimensional image of the anterior eye Ec.

Figure 6A:
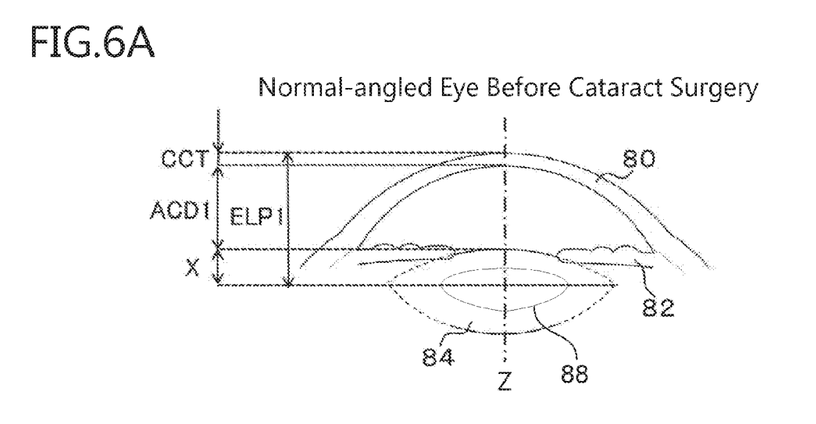
FIG. 6A is a diagram showing a calculation of an ELP by using an ACD, in a case of a patient's eye being a normal-angled eye.
Figure 6B:
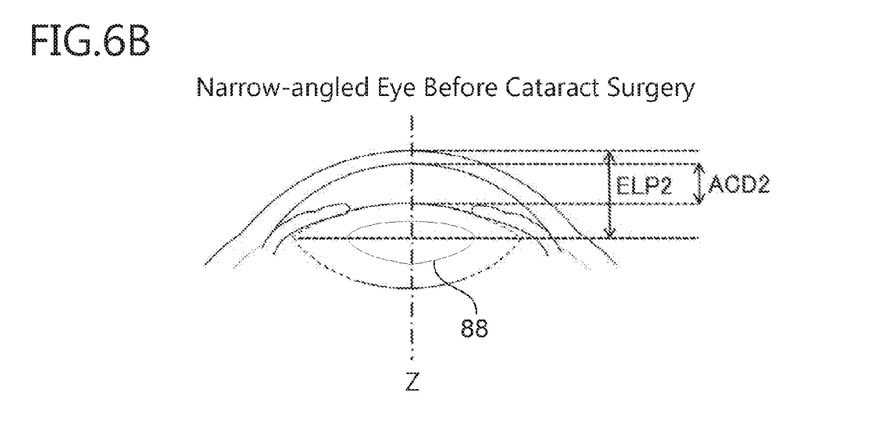
FIG. 6B is a diagram showing the calculation of the ELP by using the ACD, in a case of the patient's eye being a narrow-angled eye.
Figure 6C:
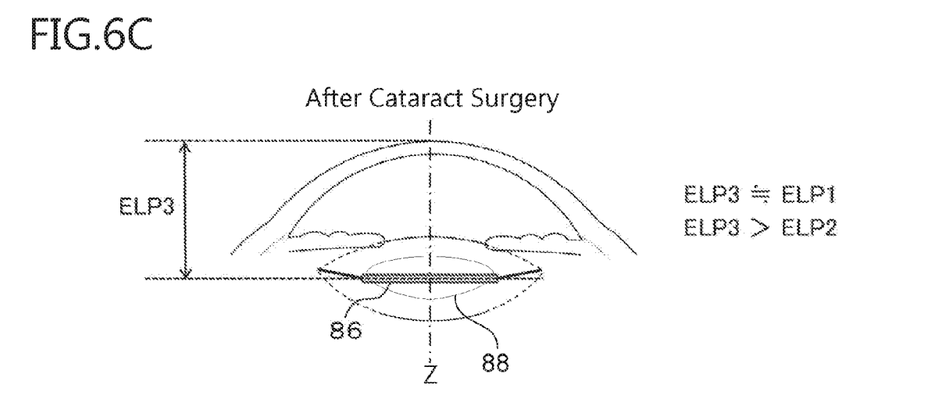
FIG. 6C is a diagram showing a state of an anterior eye after a cataract surgery.

Each of FIGS. 6A to 6C is a diagram for describing a state of each part of an anterior eye before and after a cataract surgery (an implantation of an IOL). FIGS. 6A and 6B schematically show tomographic images of the preoperative anterior eye, and FIG. 6C schematically shows a tomographic image of the postoperative anterior eye.

FIG. 6A shows a tomographic image of the preoperative anterior eye that has a normal angle (area where a rear surface of a cornea 80 intersects with a front surface of an iris 82) or an open angle even with cataract. Japanese Patent Application Publication No. 2013-94410 discloses a calculation method of an ELP 1 from tomographic images of an anterior eye, by adding a distance X, which is from a front surface of a crystalline lens 84 to a contact point of a Zinn's zonule and the crystalline lens 84, to a corneal thickness CCT and to an ACD 1 (a distance from the rear surface of the cornea 80 to the front surface of the crystalline lens 84).

However, a subjected eye does not always have the normal angle or the open angle as shown in FIG. 6A. A subjected eye may have a narrow angle as shown in FIG. 6B. In the subjected eye having the narrow angle as shown in FIG. 6B, the crystalline lens 84 is located anteriorly, and thus an ACD 2 is small compared to the eye with the normal angle shown in FIG. 6A. Accordingly, an ELP 2 obtained by the calculation is small as well.

However, it is known as a postoperative finding that even if the subjected eye has the narrow angle as shown in FIG. 6B, the narrow angle is eliminated after the cataract surgery (the implantation of the IOL) and becomes a normal state as shown in FIG. 6C.

Thus, in the case where the subjected eye has the normal angle or the open angle, the method disclosed in Japanese Patent Application Publication No. 2013-94410 is effective because the obtained ELP 1 is substantially equal to an ELP 3 shown in FIG. 6C which is a postoperative distance from the front surface of the cornea to a position of an intraocular lens 86. However, in the case where the subjected eye has the narrow angle as shown in FIG. 6B, the calculated ELP 2 is significantly small compared to the ELP 3 shown in FIG. 6C. Due to this, there is a possibility that the calculated ELP 2 and ELP 3 have a large difference therebetween.

As described hereinbelow, in the present disclosure, a position of a SS of the subjected eye which is obtained by analyzing the anterior eye tomographic images acquired by the optical coherence tomographic apparatus 1 is used instead of the ACD when the ELP is calculated. The SS position of the subjected eye is constant regardless of a state of the angle. Due to this, the ELP calculated by the method of the present disclosure is not affected by a state of the angle. Accordingly, a highly accurate ELP can be calculated for any subjected eyes.

Figure 7:
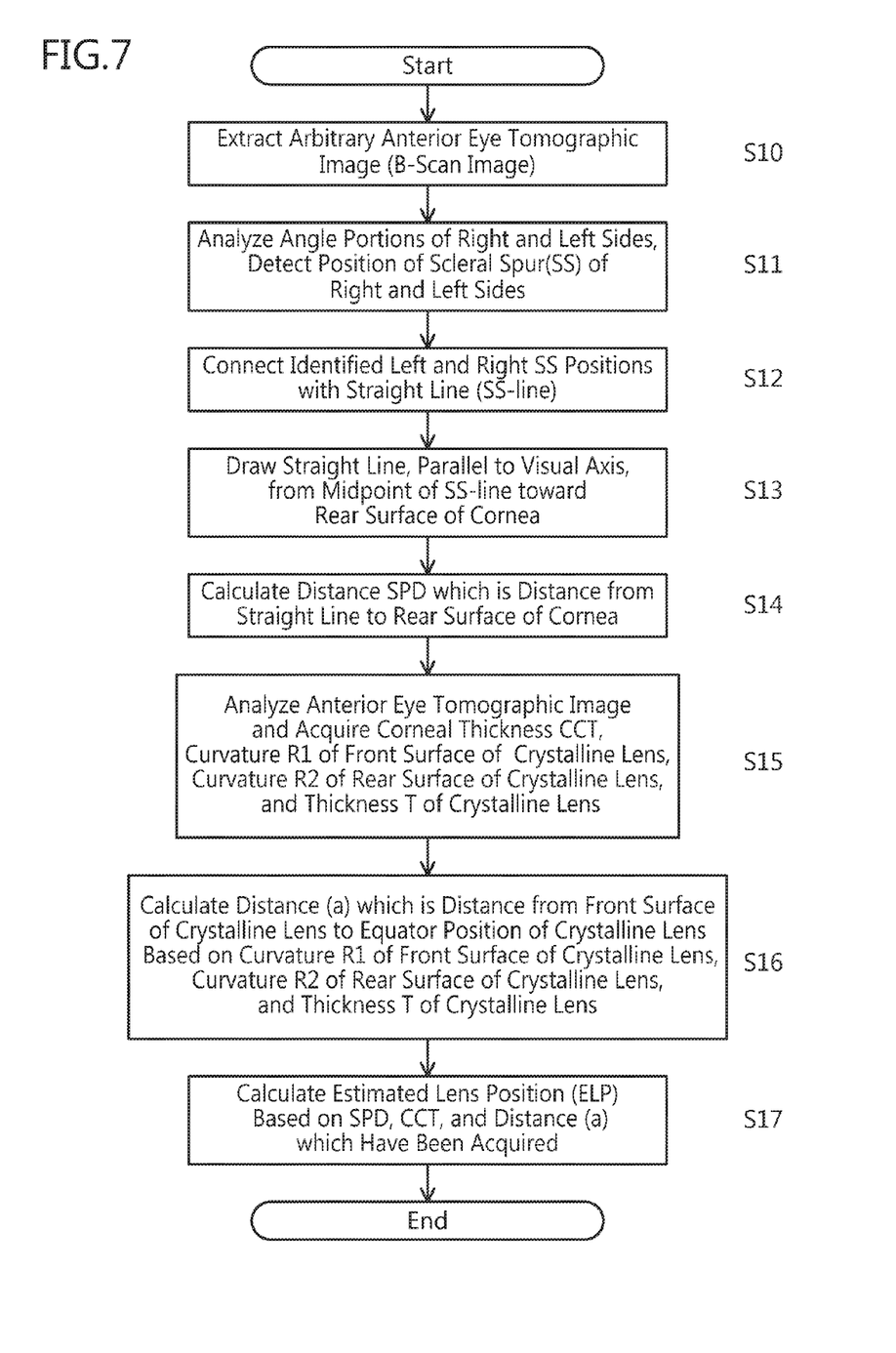
FIG. 7 is a flowchart showing a calculation procedure of the ELP according to the present disclosure.

FIG. 7 is a flowchart showing a procedure of calculating an ELP according to the calculation method of the present disclosure.

In step S10, the controller 3 extracts one arbitrary B-scan image from a plurality of B-scan images (the anterior eye tomographic images including the corneal apex) stored in the memory 10. As the extraction method, for example, a method may be employed in which a B-scan image captured along a scan line extending in a horizontal direction (a 0 degrees direction) relative to the subjected eye is selectively extracted, or a method may be employed in which a contrast value is calculated by executing a simple image processing to each B-scan image of the plurality of B-scan images, and one B-scan image is extracted from B-scan images having contrast values equal to or larger than a predetermined contrast value. An optimal extraction method can be employed appropriately to extract one B-scan image.

Figure 10:
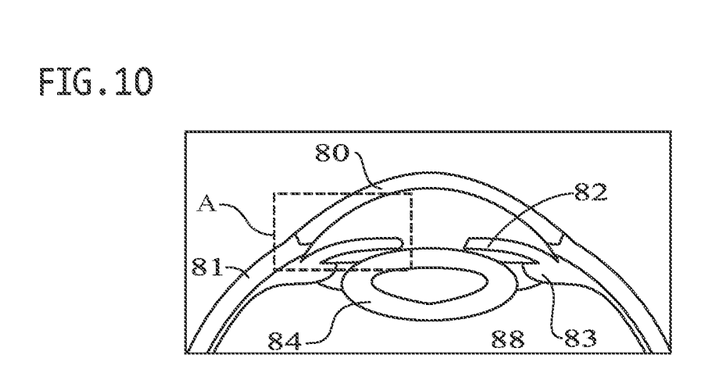
FIG. 10 is a diagram schematically showing a structure of an anterior eye.
Figure 11:
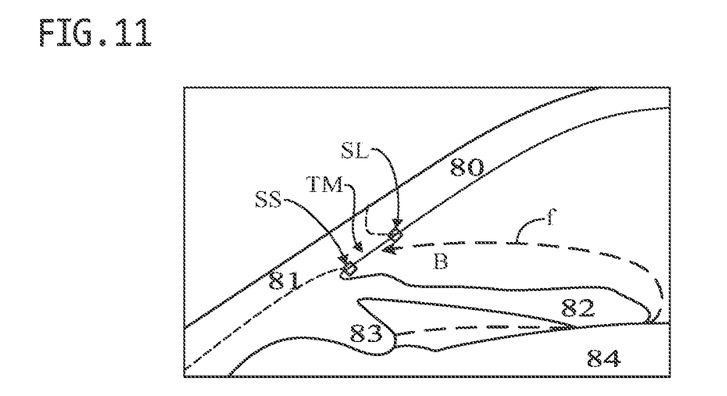
FIG. 11 is a diagram showing a structure of an angle area of the anterior eye shown by a rectangular region A in FIG. 10.

In step S11, the controller 3 analyzes angle areas positioned on right and left sides of the cornea in the extracted B-scan image, and detects a position of the SS at each side. FIG. 10 is a diagram showing a schematic structure of an anterior eye of a normal subjected eye. Then, FIG. 11 is a diagram showing a structure of an angle area of the anterior eye which is present within an area A of FIG. 10, and indicating positional relationships among the cornea 80, a scleral 81, the iris 82, a Ciliary body 83, the crystalline lens 84, the SS, a trabecular meshwork TM, and a Schwalbe's line SL. As shown in FIG. 11, the SS is located in a deep portion of the angle area of the subjected eye. In the subjected eye having the normal angle, a depth position of the SS is close to a position of an apex on the front surface of the crystalline lens 84. In the disclosure herein, the ACD (distance from the rear surface of the cornea to the apex on the front surface of the crystalline lens), which is usually measured, is calculated, however, the calculation of the ACD is not necessarily needed. The controller 3 identifies the positions of the SS, and calculates a distance between the identified SS positions and the apex on the front surface of the crystalline lens 84. Notably, methods of identifying positions of a SS from an anterior eye B-scan image are disclosed in Japanese Patent Application Publication No. 2015-66083, Japanese Patent Application Publication No. 2015-66084, and the like, and thus details thereof are omitted here.

In step S12, the controller 3 connects the identified left and right SS positions with a straight line (hereinbelow referred to as "SS-line") (see FIGS. 8A and 8B). Then, in step S13, the controller 3 draws a straight line, parallel to a visual axis Z, from a midpoint of the SS-line toward the rear surface of the cornea. In step S14, the controller 3 calculates an SPD which is a distance from a position of an intersection point of the straight line drawn in S13 and the rear surface of the cornea to the SS-line. As aforementioned, the controller 3 may calculate the ACD (distance from the rear surface of the cornea to the apex on the front surface of the crystalline lens) at this occasion. Calculating the ACD together with the SPD in step S14 makes it possible to compare values of the SPD and the ACD. For example, a state of an angle of the subjected eye (whether the subjected eye has the normal angle or the narrow angle) can be estimated by comparing the SPD value and the ACD value. Further, since there is a possibility that the calculated SPD value is incorrect if the SPD value is smaller than the ACD value beyond a predetermined range, the positions of the SS can be detected again by going back to step S11. Although the calculation of the ACD value is not necessarily needed in the method of the present disclosure, the controller 3 calculates the ACD value as well for the aforementioned reason and stores it in the memory 10.

Figure 8A:
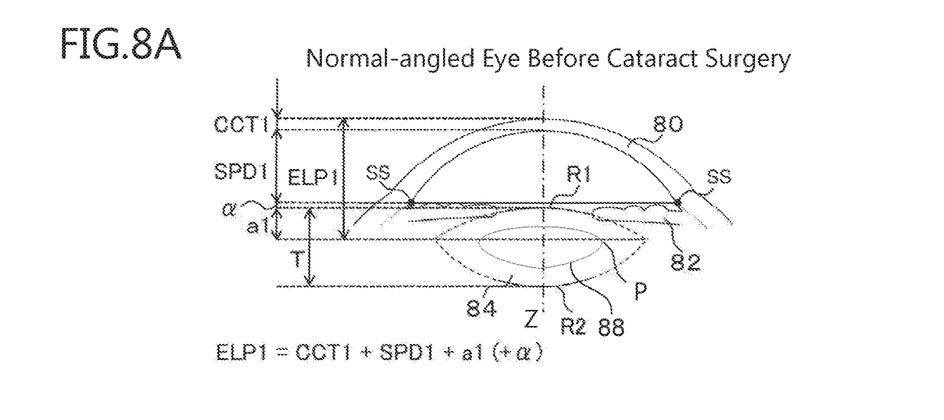
FIG. 8A is a diagram showing a calculation of the ELP by using a SS, in the case of the patient's eye being the normal-angled eye.
Figure 8B:
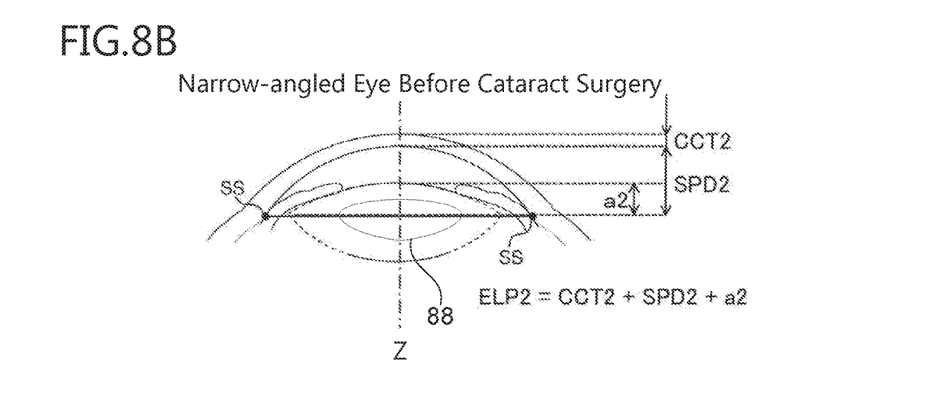
FIG. 8B is a diagram showing the calculation of the ELP by using the SS, in the case of the patient's eye being the narrow-angled eye.

In step S15, the controller 3 analyzes the anterior eye B-scan image, and acquires the corneal thickness CCT, a curvature R1 of the front surface of the crystalline lens, a curvature R2 of the rear surface of the crystalline lens, and a thickness T of the crystalline lens (see FIGS. 8A and 8B).

In step S16, the controller 3 estimates an equator position P of the crystalline lens 84 from the curvature R1, the curvature R2, and the thickness T which have been acquired in step S15, and calculates a distance (a) from the front surface of the crystalline lens to the equator position P of the crystalline lens.

Figure 9:
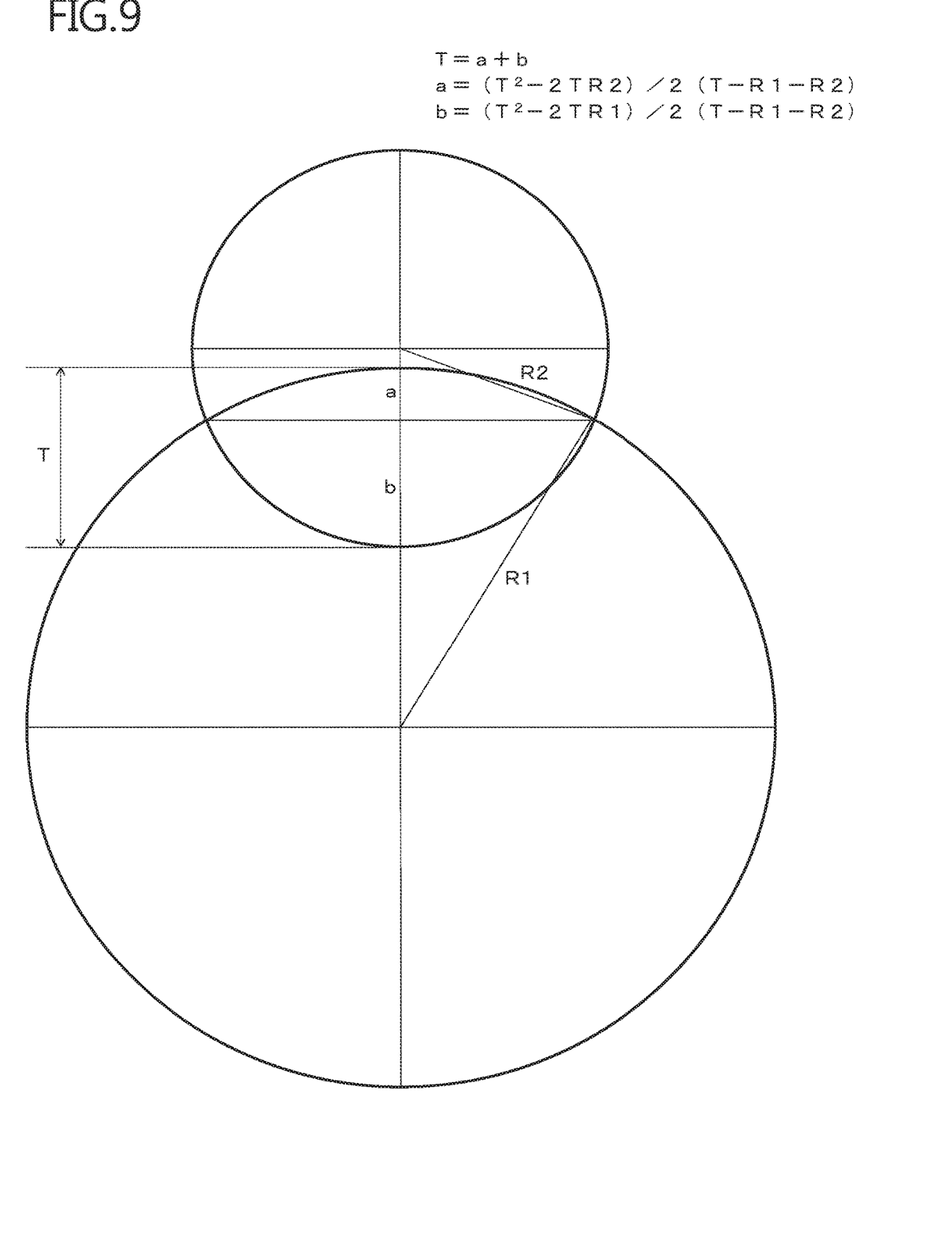
FIG. 9 is a diagram explaining an embodiment in which a lens equator is calculated from a curvature radius R1 of a front surface of a crystalline lens, a curvature radius R2 of a rear surface of the crystalline lens, and a thickness T of the crystalline lens.

FIG. 9 is a diagram explaining an embodiment of a method in which the distance (a) from the front surface of the crystalline lens to the equator position P of the crystalline lens is calculated from the curvature R1 of the front surface of the crystalline lens, the curvature R2 of the rear surface of the crystalline lens, and the thickness T of the crystalline lens. The distance (a) from the front surface of the crystalline lens to the equator position of the crystalline lens can be calculated by a presumption that a circle whose radius is the curvature R1 and a circle whose radius is the curvature R2 overlap within the thickness T of the crystalline lens as shown in FIG. 9, and a line connecting intersection points of the two circles represents the equator position of the crystalline lens. Notably, a distance (b) in FIG. 9 indicates a distance from the rear surface of the crystalline lens to the equator position P of the crystalline lens.

In step S17, the controller 3 calculates an ELP from the SPD, the CCT, and the distance (a) which have been acquired through steps S14 to S16.

The ELP calculated in step S17 of the present disclosure is applied to SRK formula or SRK/T formula, which are well-known IOL calculating formulas, as a result of which a highly accurate IOL power can be determined.

Figure 8C:
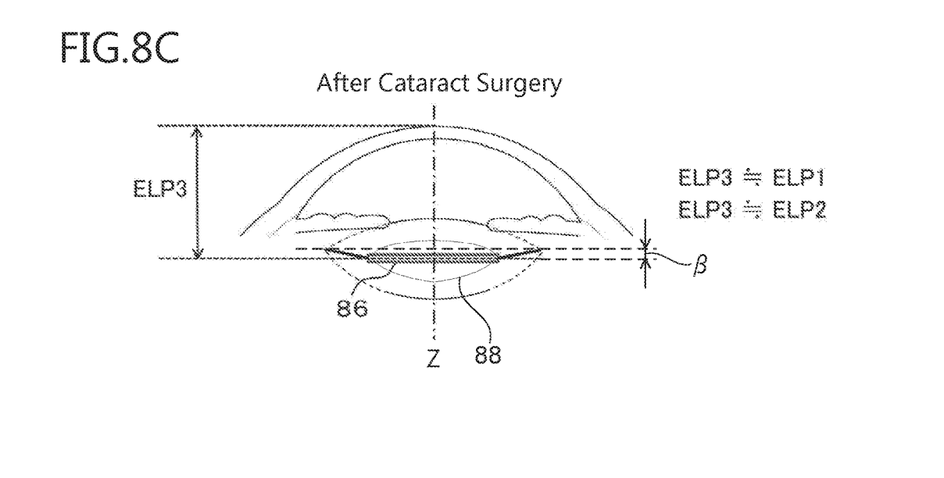
FIG. 8C is a diagram showing a state of an anterior eye after a cataract surgery.

FIGS. 8A and 8B are diagrams explaining an embodiment of a method of calculating the aforementioned ELP of the present disclosure. FIGS. 8A and 8B schematically show preoperative anterior eye tomographic images, and FIG. 8C schematically shows a preoperative anterior eye tomographic image.

FIG. 8A shows a case of a normal-angled eye. The ELP 1 in the case of the normal-angled eye can be calculated using the following formula: ELP 1=CCT 1+SPD 1+distance a1 (+α). Here, the a is a difference between the ACD 1 and the SPD 1 which have been calculated simultaneously. Although the a is not necessarily needed, it may be added as needed if the ACD 1 and the SPD 1 largely differ from each other.

FIG. 8B shows a case of a narrow-angled eye. The ELP 2 in the case of the narrow-angled eye can be calculated using the following formula: ELP 2=CCT 2+SPD 2+distance a2. Here, values of the CCT 2, the SPD 2, and the distance a2 are substantially equal to values of the CCT 1, the SPD 1, and the distance a1 of the normal-angled eye shown in FIG. 8A. Due to this, a value of the calculated ELP 2 is substantially equal to a value of the ELP 1 of the normal-angled eye shown in FIG. 8A. That is, an ELP can be calculated eliminating the difference caused by a state of angle of the subjected eye (patient's eye). Thus, regardless of the state of angle of the subjected eye (patient's eye), a highly accurate IOL power can be determined.

Embodiments of the present disclosure have been described in detail, however, it should be understood that these are mere exemplary indications and thus do not limit the scope of the claims at all by the specific descriptions thereof, these can be achieved in various aspects to which alternations, modifications, and improvements based on knowledge of those skilled in the art are added, and all of such aspects are included within the scope of the claims of the present disclosure unless they depart from the spirit of the present disclosure.

For example, in the aforementioned embodiments, the SS positions are identified by analyzing the anterior eye B-scan image in step S11. However, the SS positions are visually cognized on the anterior eye B-scan image. Thus, the examiner may designate the SS positions relative to the tomographic image T of the anterior eye angle areas displayed on the monitor 7 via the touch panel 9 and the like, the designated positions may be stored in the memory 10, and the value may be used.

Further, the position of the corneal apex, the corneal thickness, the thickness T of the crystalline lens, the depth position of the SS, the equator position of the crystalline lens and the like may be calculated based on "vertex normal", "line of sight", "pupillary axis", "fixation axis" or the like instead of visual axis Z.

Further, in the aforementioned embodiments, the equator position of the crystalline lens 84 is calculated from the curvature R1 of the front surface, the curvature R2 of the rear surface, and the thickness T of the crystalline lens 84 of the subjected eye (patient's eye). However, a calculation method of the equation position of the crystalline lens 84 is not limited thereto. For example, there is a case where the curvature R1 of the front surface, the curvature R2 of the rear surface, and the thickness T of the crystalline lens cannot be calculated accurately, if a part of the crystalline lens 84 in the anterior eye tomographic image T (B-scan image) is missing, or its shape is unclear. In this case, the equator position of the crystalline lens can be estimated by using a crystalline lens nucleus 88 of the crystalline lens 84 in the B-scan image. For example, the equator position of the crystalline lens 84 may be estimated from a shape of the crystalline lens nucleus 88 obtained by tracing the crystalline lens nucleus 88 within the crystalline lens in the acquired B-scan image (displayed on the monitor 7) automatically or manually (with a touch pen and the like).

Further, as apparent in FIG. 6C and FIG. 8C, the implanted intraocular lens (IOL) 86 is steadily placed slightly below the preoperative equator position P of the crystalline lens 84 (FIGS. 6A, 6B, 8A, and 8B). Terming a distance from the equator position to the IOL 86 as a distance β, the distance β can be obtained empirically or logically from a lens constant provided by a manufacturer of an IOL to be implanted (used in the surgery). Specifically, the operator inputs the lens constant of the IOL to the optical coherence tomographic apparatus 1, and the controller 3 identifies an implantation position of the IOL by using the lens constant and calculates the distance β. Then, the controller 3 may calculate the ELP by using the distance β which is determined for each IOL as a predetermined offset value. By using such offset value, a further highly accurate ELP can be calculated.

Further, ELPs may be calculated from two or more B-scan images respectively, and an average value of those ELPs may be used as the ELP. In this case, the plurality of B-scan images may be a plurality of B-scan images that have been captured along different scan-lines in one measurement, or may be a plurality of B-scan images that have been captured along a same scan-line in plural measurements. By using the plurality of B-scan images, a further highly accurate ELP can be calculated.

Further, in the aforementioned embodiments, the three-dimensional images of the anterior eye are acquired by the radial scan (in which each scan line passes through the corneal apex) as shown in FIG. 5. That is, a three-dimensional distribution of the SS positions can be measured by identifying the SS positions relative to each B-scan image. Then, the SPD in the aforementioned embodiments may be calculated from a distance between a plane formed by the measured SS positions (points) and the corneal apex. By using the SPD calculated in such method, accuracy of the ELP can be improved.

What is claimed is:

1. An anterior eye tomographic image capturing apparatus configured to determine a power of an intraocular lens (IOL), the apparatus comprising:
  a processor; and
  a memory storing computer-readable instructions therein, the computer-readable instructions, when executed by the processor, causing the apparatus to perform:
  acquiring a tomographic image of an anterior eye along a straight line passing through a corneal apex of the anterior eye;
  identifying a corneal apex position of the anterior eye, an equator position of a crystalline lens of the anterior eye, and a scleral spur (SS) position of the anterior eye based on the tomographic image, wherein the SS position is located in an angle area of the anterior eye on an anterior side of the iris at a boundary between the scleral and ciliary bodies; and
  calculating an estimated lens position (ELP) based on a first distance from the corneal apex position to the SS position in a direction of a visual axis and a second distance from the SS position to the equator position in the direction of the visual axis to determine the power of the IOL.

2. The anterior eye tomographic image capturing apparatus as in claim 1, wherein the identifying comprises:
  identifying a thickness of the crystalline lens in the direction of the visual axis at a position that overlaps with the visual axis, a first curvature of a front surface of the crystalline lens, and a second curvature of a rear surface of the crystalline lens based on the tomographic image; and
  identifying the equator position of the crystalline lens based on the thickness of the crystalline lens, the first curvature, and the second curvature.

3. The anterior eye tomographic image capturing apparatus as in claim 1, wherein the identifying comprises:
  identifying a crystalline lens nucleus of the crystalline lens based on the tomographic image; and
  identifying the equator position of the crystalline lens based on the crystalline lens nucleus.

4. The anterior eye tomographic image capturing apparatus as in claim 1, wherein the identifying comprises:
  identifying a thickness of the crystalline lens in the direction of the visual axis at a position that overlaps with the visual axis, a first curvature of a front surface of the crystalline lens, and a second curvature of a rear surface of the crystalline lens based on the tomographic image;
  identifying a first equator position based on the thickness of the crystalline lens, the first curvature, and the second curvature;

identifying a crystalline lens nucleus of the crystalline lens based on the tomographic image;

identifying a second equator position based on the crystalline lens nucleus; and identifying the equator position based on at least one of the first equator position and the second equator position.

5. The anterior eye tomographic image capturing apparatus as in claim 1, wherein the identifying comprises:

identifying an implantation position of the IOL in a case where the IOL is to be implanted to the crystalline lens of the anterior eye, and the calculating comprises:

calculating a third distance from the IOL to the equator position in the direction of the visual axis; and calculating the ELP using the first distance, the second distance, and the third distance.

6. A non-transitory computer-readable recording medium storing computer-readable instructions for an anterior eye tomographic image capturing apparatus, the computer-readable instructions, when executed by a processor of the anterior eye tomographic image capturing apparatus, causing the anterior eye tomographic image capturing apparatus to execute:

acquiring a tomographic image of an anterior eye along a straight line passing through a corneal apex of the anterior eye;

identifying a corneal apex position of the anterior eye, an equator position of a crystalline lens of the anterior eye, and a scleral spur (SS) position of the anterior eye based on the tomographic image, wherein the SS position is located in an angle area of the anterior eye on an anterior side of the iris at a boundary between the scleral and ciliary bodies; and calculating an estimated lens position (ELP) based on a first distance from the corneal apex position to the SS position in a direction of a visual axis and a second distance from the SS position to the equator position in the direction of the visual axis of determine power of an intraocular lens (IOL).

7. An apparatus comprising:

a processor; and a memory storing computer-readable instructions therein, the computer-readable instructions, when executed by the processor, causing the apparatus to perform:

acquiring a tomographic image of an anterior eye along a straight line passing through a corneal apex of the anterior eye;

identifying a corneal apex position of the anterior eye, an equator position of a crystalline lens of the anterior eye, and a scleral spur (SS) position of the anterior eye based on the tomographic image, wherein the SS position is located in an angle area of the anterior eye on an anterior side of the iris at a boundary between the scleral and ciliary bodies; and calculating an estimated lens position (ELP) based on a first distance from the corneal apex position to the SS position in a direction of a visual axis and a second distance from the SS position to the equator position in the direction of the visual axis to determine power of an intraocular lens (IOL).

* * * * *